United States Patent [19]

Holtkamp, Sr.

[11] Patent Number: Plant 6,525

[45] Date of Patent: Jan. 10, 1989

[54] AFRICAN VIOLET PLANT NAMED MOLOKAI

[75] Inventor: Reinhold Holtkamp, Sr., Isselburg, Fed. Rep. of Germany

[73] Assignee: Gessellschaftsvertrag uber die Erfindergemeinschaft "Optimara", Rees Haffen, Fed. Rep. of Germany

[21] Appl. No.: 55,877

[22] Filed: Jun. 1, 1987

[51] Int. Cl.[4] ..... A01H 5/00

[52] U.S. Cl. ..... Plt./69

[58] Field of Search ..... Plt./69

*Primary Examiner*—Robert E. Bagwill

*Attorney, Agent, or Firm*—Foley & Lardner, Schwartz, Jeffery, Schwaab, Mack, Blumenthal & Evans

[57] ABSTRACT

An African violet plant named Molokai, characterized by its light violet blue flowers which have a darker center and which fade out to a white edge; first flash of flowers forming a tight bouquet above the leaves on strong upright flower stems curving toward the center; profuse flowering; vigorous growth habit; dark green, serrated, velvety leaves, slightly hairy; long lasting and non-dropping flowering habit.

1 Drawing Sheet

The present invention comprises a new and distinct cultivar of African violet plant, botanically known as *Saintpaulia ionantha,* and hereinafter referred to by the cultivar name Molokai.

The new cultivar was referred to during the breeding and selection process by the designation H79/3, and is a product of a planned breeding program. The new cultivar was originated from a cross made by applicant in a controlled breeding program in Haffen, Federal Republic of Germany. The female, or seed parent was a cultivar designated 69M Carolina red. The male, or pollen parent was a cultivar designated GG181 Blue.

Molokai was discovered and selected by me as a flowering plant within the progeny of the stated cross in a controlled environment in Haffen, Federal Republic of Germany. Asexual reproduction of the new cultivar by leaf cuttings, as performed by me at Haffen, Federal Republic of Germany, has demonstrated that the combination of characteristics as herein disclosed for the new cultivar are firmly fixed and retained through successive generations of asexual reproduction.

Molokai has not been observed under all possible environmental conditions. The phenotype may vary significantly with variations in environment such as temperature, light intensity and day length. The following observations, measurements and values describe the new cultivar as grown in 10 cm pots in Haffen, Federal Republic of Germany and Nashville, Tenn. under greenhouse conditions which closely approximate those generally used in commercial practice.

The following traits have been repeatedly observed and are determined to be basic characteristics of Molokai which in combination distinguish this African violet as a new and distinct cultivar:

1. Relatively light violet blue flowers fading out to a white edge.
2. First flash of flowers forms a tight bouquet above the leaves on strong upright flower stems.
3. Each plant carries 8 or more upright flower stems, each of which carries 10 to 12 flowers.
4. Profuse flowering.
5. Seed capsule pushes slightly through.
6. Vigorous grower.
7. Plant saleable 10–11 weeks after potting.
8. Dark green, serrated, velvety leaves, slightly hairy.

9. After maturity, the flowers dry off and remain on the peduncle without becoming infected by botrytis.
10. Long-lasting, non-dropping single flowers.

The accompanying color photographic drawing shows a typical specimen plant of the new cultivar. The colors appearing in the photograph are as true as possible with color illustrations of this type.

In the following description, color references are made to The Royal Horticultural Society Colour Chart (RHS), except where general colors of ordinary significance are referred to. Color values were taken under natural light conditions at approximately 1:00 p.m. in Nashville, Tenn. Under cooler growing conditions and more intensive lighting, the light blue color becomes more intense.

Botanical classification: *Saintpaulia ionantha,* Ramat., cv. Molokai.

Parentage:

*Male parent.*—GG181 Blue.

*Female parent.*—69M Carolina red.

Propagation: The new cultivar holds its distinguishing characteristics through successive propagations by leaf cuttings and by division of shoots.

Plant: From 10 cm to 12 cm tall when grown in pots, and approximately 22–25 cm in diameter when fully grown. The growth rate is vigorous.

*Leaves.*—Shape: Oval. Diameter: 65–70 mm wide and 85–95 mm long. Texture: Velvety. Aspect: Serrated, hairy. Ribs and veins: Upperside visible, underside very well pronounced, light green and shiny. Color (upper side): Green 137A. Color (under side): Red purple between veins; light green veins. Petiole: Strong, upright, purplish, hairy.

*Flowers.*—Buds: Bell-shaped, 8–10 mm before opening. Sepals: Five (5) in number, purplish-brown. Calyx: Funnel-shaped. Aspect: Spear-shaped, hairy. Peduncle: Strong, upright, purplish brown, hairy.

*Individual flowers.*—Size: 35 to 40 mm. Shape: Single violet-shaped, slightly waved. Color (upper side): Violet blue 91A-B, with white margins (barely visible in photograph); darker in center, approximately 90A-B. Color (under side): Violet blue 97A-B, with white margins. Borne: Each flower stem carries 10–12 flowers each on strong, upright, wirelike peduncles that are free standing above the leaves. Flowering habit: Flowers 9–10 weeks after potting; flowering very profuse. Corolla: Compact flower head.

*Reproductive organs.*—Stamens: Two (2) in number. Anthers: Two stamens composed of 4 anther cells. Filaments: 5 mm long, yellowish green. Pollen Color: Yellow 7A. Styles: 7 mm, purplish blue.

*Roots.*—Normally developed, white when young, turning slightly brownish when older.

Disease resistance: Good.

General observations: Molokai is a vigorous grower, with attractive dark green, serrated leaves. Out of the center, 8 and more strong flower stems appear that are slightly bending toward the center, carrying 10–12 and more single, violet-shaped flowers. The flowers are violet blue with a darker violet blue in the center. The violet blue color fades out to white at the slightly wavy edges. Approximately 10–11 weeks after potting the plant is saleable. The flowers are long-lasting and non-dropping and the seed capsule pushes through.

I claim:

1. A new and distinct cultivar of African violet named Molokai, as described and illustrated, and particularly characterized by its light violet blue flowers which have a darker center and which fade out to a white edge; first flash of flowers forming a tight bouquet above the leaves on strong upright flower stems curving toward the center; profuse flowering; vigorous growth habit; dark green, serrated, velvety leaves, slightly hairy; and long lasting and non-dropping flowering habit.

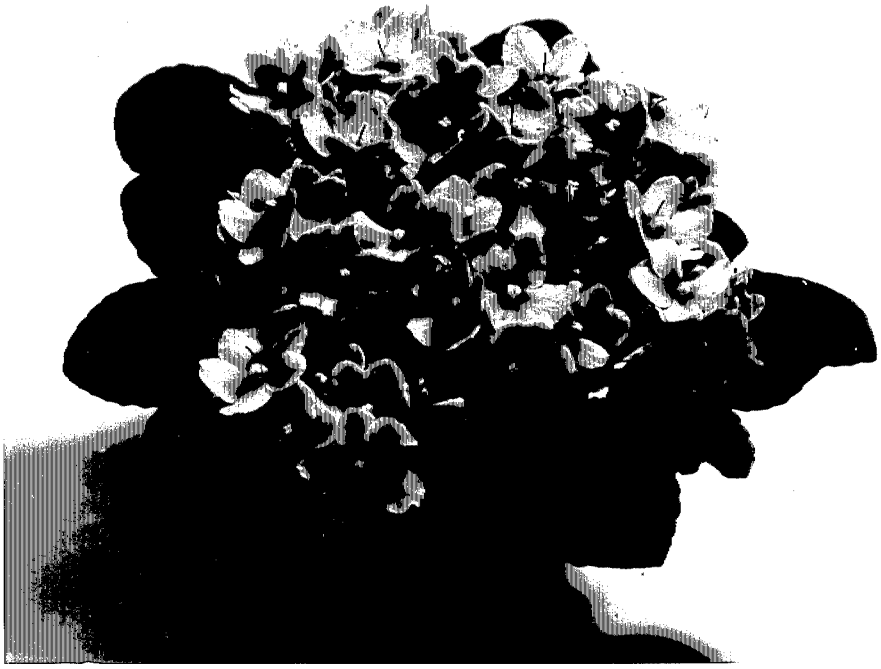
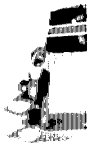

* * * * *